United States Patent
Boston

[19]

[11] Patent Number: 6,106,291

[45] Date of Patent: Aug. 22, 2000

[54] SELECTIVE DENTIN CARIES EXCAVATOR

[75] Inventor: Daniel W. Boston, St. Davids, Pa.

[73] Assignee: Temple University of the Commonwealth System of Higher Education, Philadelphia, Pa.

[21] Appl. No.: 09/211,402

[22] Filed: Dec. 15, 1998

[51] Int. Cl.⁷ ..................................................... A61C 3/02
[52] U.S. Cl. ........................................... 433/165; 433/166
[58] Field of Search .................................... 433/125, 165, 433/166, 229

[56]   References Cited

U.S. PATENT DOCUMENTS

| 463,619 | 11/1891 | Burdick . |
| 503,744 | 8/1893 | How . |
| 706,013 | 8/1902 | Boyce ..................................... 433/165 |
| 1,225,230 | 5/1917 | Elwin . |
| 1,636,577 | 7/1927 | Schuller . |
| 4,190,958 | 3/1980 | Martin et al. . |
| 4,283,175 | 8/1981 | Nash . |
| 4,365,958 | 12/1982 | Vlock . |
| 4,449,937 | 5/1984 | Weissman . |
| 4,571,184 | 2/1986 | Edwardson .............................. 433/166 |
| 4,661,061 | 4/1987 | Martin . |
| 4,684,346 | 8/1987 | Martin . |
| 4,709,480 | 12/1987 | Takigawa et al. . |
| 5,017,137 | 5/1991 | Weissman . |
| 5,035,618 | 7/1991 | Katz et al. . |
| 5,299,937 | 4/1994 | Gow . |
| 5,316,475 | 5/1994 | Rosenberg ............................... 433/166 |
| 5,601,430 | 2/1997 | Kutsch et al. . |
| 5,636,983 | 6/1997 | Shoji et al. . |
| 5,676,593 | 10/1997 | Stevens . |
| 5,779,476 | 7/1998 | Roetzer .................................... 433/166 |
| 5,882,201 | 3/1999 | Salem .................................. 433/166 X |

FOREIGN PATENT DOCUMENTS 2 303 148   7/1974   Germany .

OTHER PUBLICATIONS

"Rotary Cutting Instruments," The Art and Science of Operative Dentistry, Third Edition, pp. 345–352, 1995.

"Surgical Carbide Burs," Advertisement for Karl Schumacher Dental Instrument Co., 1998.

*Primary Examiner*—Nicholas D Lucchesi
*Attorney, Agent, or Firm*—Ratner & Prestia

[57]   ABSTRACT

A dental bur has a working surface including cutting elements which deflect or abrade upon encountering material at or above the preselected hardness corresponding to the lower limit of hardness of non-carious dentin. The dental bur is constructed of metal, ceramic, or plastic.

18 Claims, 4 Drawing Sheets

SELECTIVE DENTIN CARIES EXCAVATOR

FIELD OF THE INVENTION

This invention relates generally to the field of dental cutting tools, and more specifically to a dental bur that selectively removes carious dentin without removing healthy dentin.

BACKGROUND OF THE INVENTION

There are many common dental instruments used for removing carious dentin from teeth. Typically, however, unless the operator senses when a harder material is encountered and immediately ceases drilling, prior art burs will continue to cut into normal dentin during and after removal of the carious dentin. Because of the difficulty in sensing precisely when harder material is encountered, the side effect of using such a bur is some cutting of normal healthy dentin. In addition, this produces an infected and clogged bur that is relatively expensive to discard and difficult to sterilize.

It is therefore an object of the present invention to provide a dental cutting tool capable of selectively differentiating between harder and softer material, substantially irrespective of operator control.

SUMMARY OF THE INVENTION

The dental cutting tool (or "bur") of the present invention has a working surface that includes cutting elements adapted to cut or drill selectively only material of less than a preselected hardness. When material above the preselected level of hardness is encountered, the cutting elements deflect, deform, or abrade, thus preventing damage to the harder non-carious dentin.

BRIEF DESCRIPTION OF THE DRAWING

The invention is best understood from the following detailed description when read in connection with the accompanying drawings, in which.

DETAILED DESCRIPTION OF THE INVENTION

Figure 1:
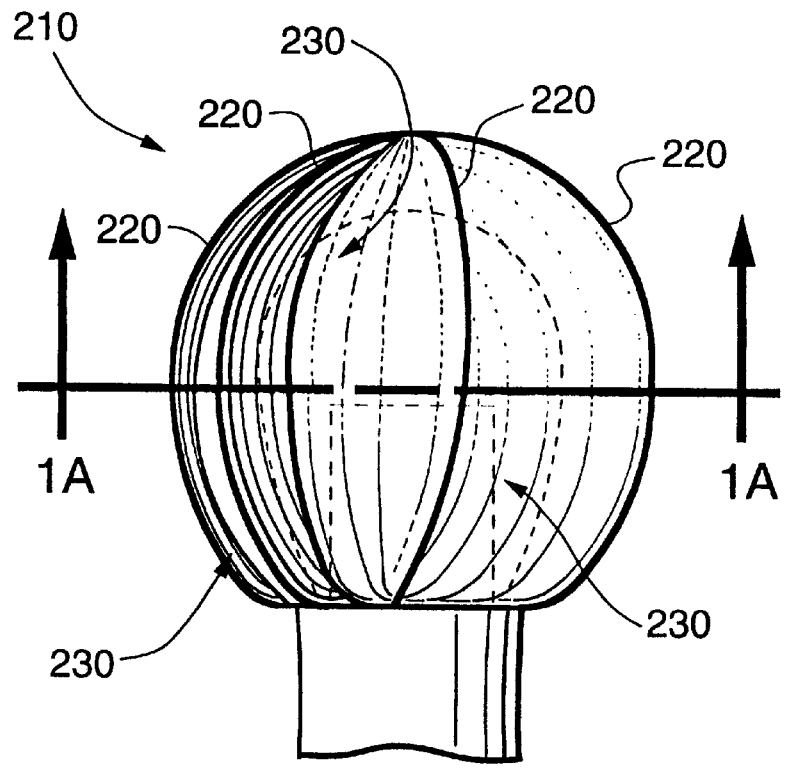
FIG. 1 is a side view of a dental bur formed according to a first embodiment of the present invention.
Figure 1A:
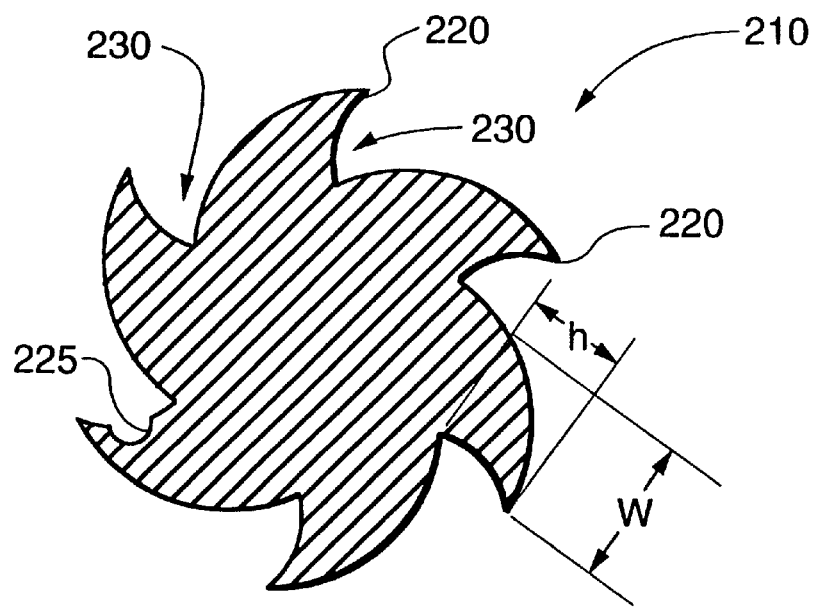
FIG. 1A is a sectional view, in the plane 1A—1A, of the bur shown in FIG. 1.

Referring now to the Figures, wherein like reference numerals refer to like steps and elements throughout, FIGS. 1 and 1A are side and sectional views, respectively, of the cutting head of a bur according to the first exemplary embodiment of the present invention. As shown in FIGS. 1 and 1A, bur 210 includes bur blades 220 interposed between grooves 230. Bur blades 220 are formed so that they will cut soft carious dentin, but will bend inward into the space of grooves 230 upon reaching a dentin of a specified hardness and render bur 210 temporarily or permanently inoperable. Optimally, blades 220 may include concavity 225 to effect better control of the deflection, deformation, and/or abrasion of blades 220 upon encountering a resistant force above a preselected level, characteristic of the maximum force needed to cut carious dentin, without cutting healthy dentin. This may vary with different individual situations, patients, or patient groups but, generally, the lower level of hardness for normal dentin is in the range of about 20 to about 60 Knoop Hardness Number (KHN). Thus, the blades (or cutting elements in other embodiments) of the present invention would be constructed so as to deflect, deform, or abrade upon encountering material above a preselected hardness, preferably above 60 KHN.

Skilled designers can readily design blades 220 so as to deflect at the preselected resistant force by proper selection of the material of construction of blades 220, and the dimensions thereof, particularly the height of each blade and the varying width of each blade. In addition, as indicated above, concavities 225 can be incorporated into the design of the blades 220 to optimize deflection or deformation.

The number of bur blades 220 can be increased or reduced according to design parameters. Similarly, the depth of grooves 230 can be varied and the surface area of bur blades 220 can be increased or decreased according to specific design parameters. For example, the number of bur blades 220 can be reduced and grooves 230 can be deepened to increase the scooping effect in soft dentin, and to decrease the efficiency of bur blades 220 as the bur approaches harder material.

Still another important design variable, which the skilled designer will optimize for optimum performance is concavity 225, the slope and depth of which may vary considerably. For example, an angular indentation may also perform this deflection-effecting function (i.e., to control the resistance level at which bur blade 220 will defect).

Certain embodiments of bur blades 220 can recover to their initial shape after bending back into grooves 230 and may be available then to cut more superficial, softer carious dentin. These include silicone rubber and resilient, molded plastic embodiments. The ability to recover allows for removal of carious dentin by multiple vertical approaches. In other alternative embodiments of bur 210, constructed of aluminum, aluminum alloy, hard ceramic, and plastic, blades 220 will deform or abrade and be rendered inoperable.

The shape of blades 220 and grooves 230 may be better seen from the cross sectional view of bur 210 in FIG. 1A. Bur 210 may be manufactured by machining a relatively hard metal sphere, such as one comprised of aluminum or aluminum alloy. Alternatively, blades 220 may be separately formed and secured to an underlying base. In either case, blades 220 may be anchored through a shank to a central pin extending through blades 220 and the core.

The shank is standard sized, such as described in American National Standards Institute/American Dental Association (ANSI/ADA) Specification No. 23 (dental excavating burs). The shank may be constructed of steel, aluminum, or other suitable materials. Both latch type (Class 1-Angle handpiece) and friction grip (Class 4-Angle handpiece) shanks may be used in the excavator of the present invention. Bur 210 may also be injection molded from liquid silicone rubber for example.

The color of bur 210 can be made unique for each size bur and for each hardness level at which bur 210 is molded. This allows the user of bur 210 to identify quickly the desired size and hardness level of the bur needed. The head of the bur can be spherical or egg-shaped, having a diameter between about 0.6 mm and about 4.0 mm. In addition, the head can have alternative shapes that are compatible with the cutting elements of the present invention. The head can be made out of a variety of materials, including molded plastic, optionally polymethylmethacrylate, silicone rubber, wire ball, polymer wool, aluminum or aluminum alloy, cast alloy, and ceramic.

As an alternative to the design of blades 220 which deflect upon encountering a preselected resistance force, bur blades 220 may be composed of an abradable material, such as hard ceramic elements embedded in a resinous base, designed to fracture or release the ceramic element when the preselected resistance force is encountered. Bur 210 may also be machinable from a hard ceramic material or injection molded from plastic material.

Still other characteristics may be designed into blades 220 by increasing or decreasing the distance between consecutive blades 220 and, thus, enlarging or reducing the area of the grooves where blades 220 may retract.

Figure 2:
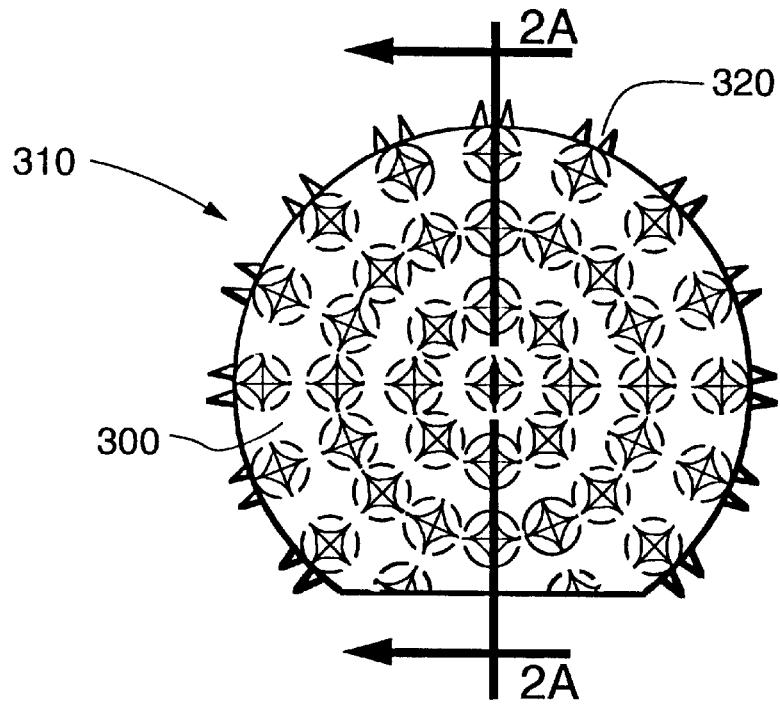
FIG. 2 is a side view of a bur formed according to a second exemplary embodiment of the present invention.
Figure 2A:
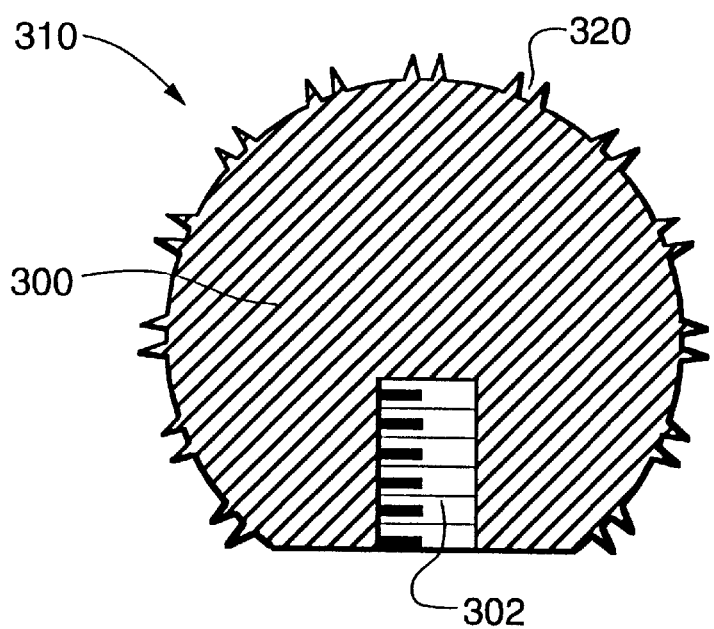
FIG. 2A is a sectional view, in the plane 2A—2A, of the bur shown in FIG. 2.
Figure 3:
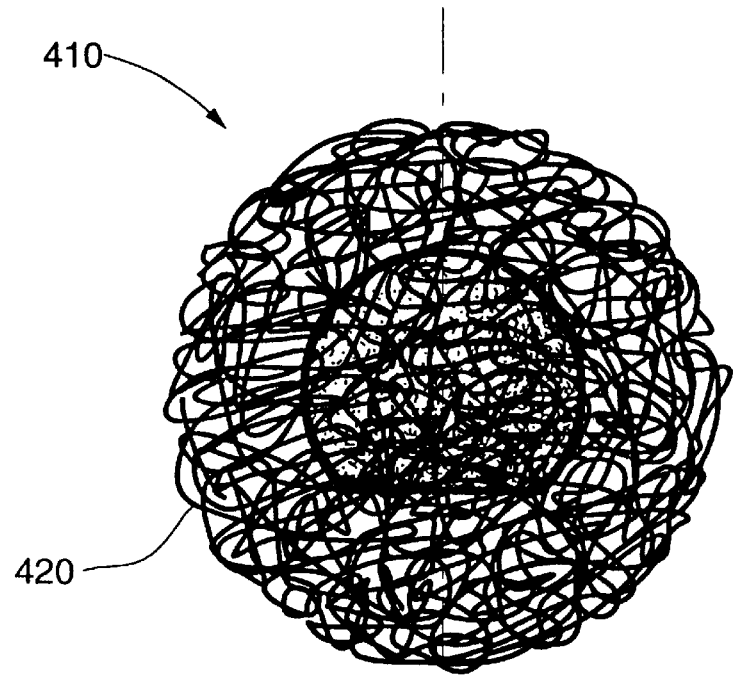
FIG. 3 is a side view of a bur formed according to a third exemplary embodiment of the present invention.
Figure 5:
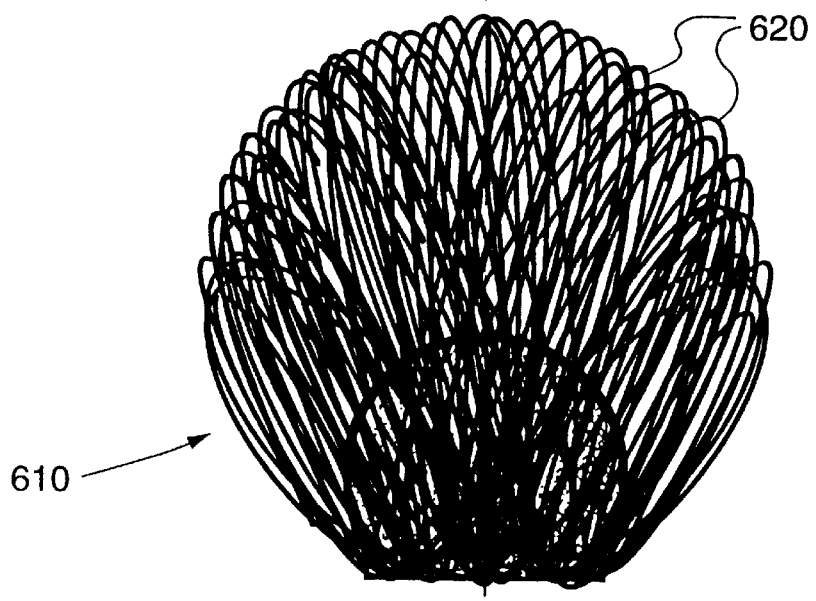
FIG. 5 is a side view of a bur formed according to a fifth exemplary embodiment of the present invention.
Figure 4:
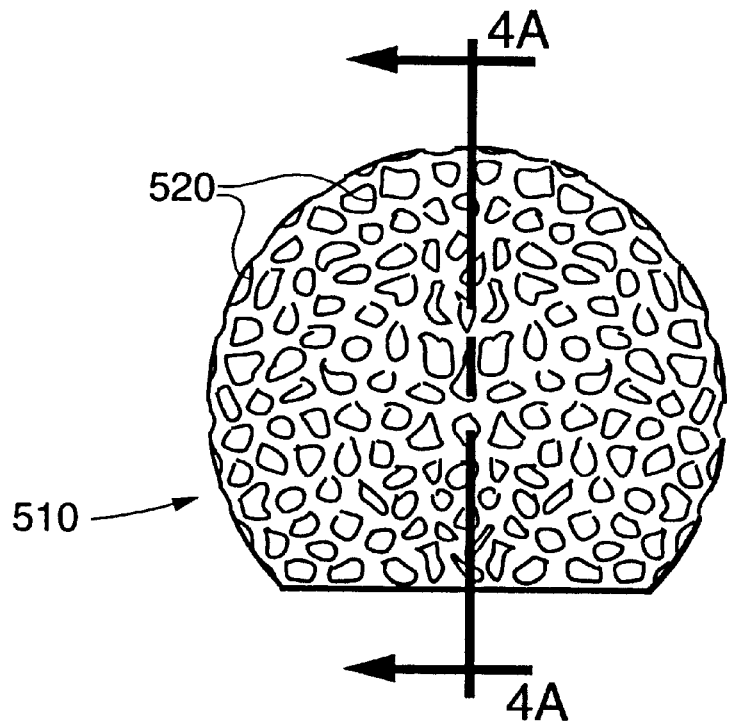
FIG. 4 is a side view of a bur formed according to a fourth exemplary embodiment of the present invention.
Figure 4A:
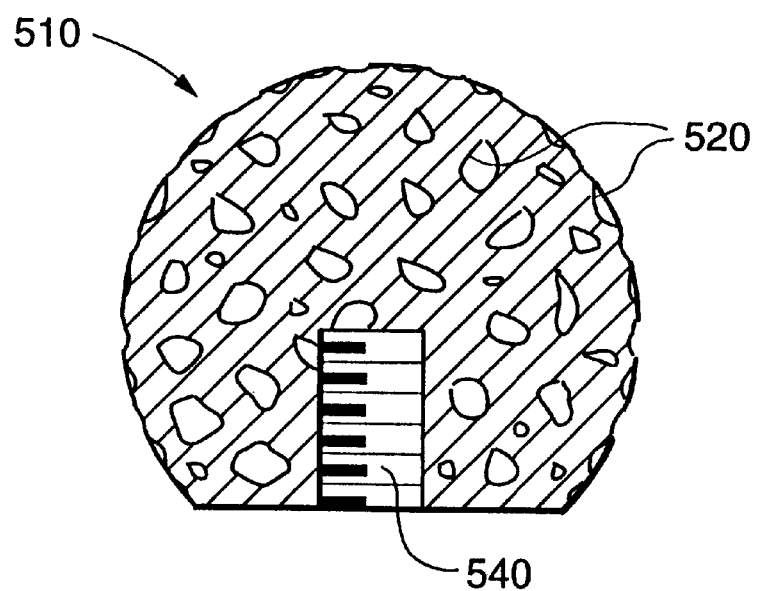
FIG. 4A is a sectional view, in the plane 4A—4A, of the bur shown in FIG. 4.

Still other alternative bur designs are shown, for example, in FIG. 2, a side view of bur 310 formed according to a second exemplary embodiment of the present invention, and in FIG. 2A, a cross section of bur 310 shown in FIG. 2. FIG. 3 shows bur 410 having wires 420 in a polymer wool ball. FIG. 4 shows bur 510 in a ball like structure and FIG. 4A shows a cross section of bur 510 shown in FIG. 4. FIG. 5 shows bur 610 also having wires 620 in an alternative ball like structure.

The burs shown in FIGS. 2–5 all vary in their mechanical design but each depends on the core concept of the present invention which is the use of cutting elements that either deflect, deform, or abrade upon encountering a preselected cutting resistance force. This force is characteristic of the differential force below which soft or carious dentin may be cut or drilled by the bur and above which the cutting action would also be effective against healthy dentin.

These different mechanical forms of the present invention include, in FIGS. 2 and 2A, a ball like central element 300 with a threaded recess 302 for mounting the bur on a conventional dental drilling apparatus. Although not shown in the Figures, such a mounting recess would necessarily be included in all bur heads made of a different material than the shank, i.e., machined ceramic, molded silicone rubber, wire ball, polymer wool ball, and ceramic foam versions. Moreover, the mounting recess is not necessary when the material for the entire excavator (blades, core, and shank) is the same, i.e., machined aluminum or aluminum alloy and molded plastic versions. As described above, the shank of the excavator would conform to ANSI/ADA specifications. The dental bur 310 of FIGS. 2 and 2A further includes outwardly punched projections 320 which serve as cutting elements. Like the cutting blades of bur 210 in FIG. 1, the outward projections 320 in bur 310, of FIGS. 2 and 2A, are mechanically designed to either deflect or abrade upon encountering dentin of preselected hardness. Such a design may easily be made by those skilled in the art by reference to the dimensions and the material used in the construction of the upstanding projections, constituting cutting elements 320 in the bur of FIGS. 2 and 2A.

In addition, the embodiments, as shown in FIGS. 3 and 5, comprise dental burs wherein the cutting elements, which may be disposed over a mounting ball as in previous embodiments, comprise relatively hard, wire-like cutting material 420, in FIG. 3, or material 620, in FIG. 5. The material is sufficiently resistant to deflecting and abrading to cut softer dentin material, but sufficiently deflectable or abradable so as to avoid cutting or damaging healthy dentin material. This may be useful to avoid interruption of the cutting action in other burs in which narrow grooves in a bur 210 of the type shown in FIG. 1, or a more dense cutting material in a bur 510 of the type shown in FIG. 4, become fully loaded with carious dentin removed from the drilling surface, thus impeding a further cutting action. The cutting effectiveness of the wires shown in FIGS. 3 and 5 will be determined by the design factors of the shape resilience of the wire selected in relation to the cross section of the individual wire filaments, and the density of the bulk wire. This is a relationship of the space occupied by the wire itself versus the space occupied by the interstices surrounding the wire. Material selection will also be an important part of the design consideration in the development of cutting elements based on wire-like materials in accordance with these embodiments.

Still another embodiment of the present invention is that shown in FIGS. 4 and 4A, in which the dental bur 510 comprises a ball member with pores 520. The residual surrounding material of the pores 520 at the outer surface of the ball like bur 510 comprise cutting elements which, as in previous embodiments, are designed with respect to the material of construction and the dimensions. Ball like bur 510 also includes recess 540 for mounting bur 510 on a conventional dental drilling apparatus. A porous cutting bur 510 as shown in FIGS. 4 and 4A may also be designed specifically to provide sufficient porosity to retain carious dentin removed from the drilling surface so as to avoid interruption of the cutting process.

Although illustrated and described herein with reference to certain specific embodiments, the present invention is nevertheless not intended to be limited to the details shown. Rather, various modifications may be made in the details within the scope and range of equivalents of the claims and without departing from the invention.

What is claimed:

1. A dental bur for use in removing carious dentin from teeth, said bur having a working surface including cutting elements, said cutting elements being adapted to deflect, deform, or abrade upon encountering material having a hardness at or above a number from about 20 Knoop Hardness Number to about 60 Knoop Hardness Number, said number corresponding to the lower limit of hardness of non-carious dentin.

2. The dental bur according to claim 1, said bur being positioned on a mounting member, adapted to be retained in and activated by a dental drilling apparatus.

3. The dental bur according to claim 2, said mounting member being removably positioned on said apparatus.

4. The dental bur according to claim 3 wherein said cutting elements are external projections disposed over a ball like structure surface.

5. The dental bur according to claim 4 wherein said cutting elements are comprised of a metal.

6. The dental bur as recited in claim 5 wherein said metal is aluminum or aluminum alloy.

7. The dental bur according to claim 3 wherein said cutting elements comprise a mass of wires shaped around a ball like structure.

8. The dental bur according to claim 3 wherein said cutting elements comprise a mass of wires having a random orientation and compacted to form a ball like structure.

9. The dental bur according to claim 1 wherein said cutting elements are adapted to deflect when acted upon by a shear force in excess of that necessary to cut material at or above the lower limit of hardness of non-carious dentin.

10. The dental bur according to claim 1 wherein said cutting elements comprise a plurality of outwardly projecting blades interposed between a plurality of grooves in a ball like structure.

11. The dental bur according to claim 10 wherein said cutting elements are comprised of aluminum or aluminum alloy.

12. The dental bur according to claim 1 wherein said cutting elements arc adapted to abrade when acted upon by a shear force in excess of that necessary to cut material at or above the lower limit of hardness of non-carious dentin.

13. The dental bur according to claim 12 wherein said cutting elements comprise a plurality of blades interposed between a plurality of grooves in a ball like structure.

14. The dental bur according to claim 12 wherein said abradable cutting elements comprise a hard ceramic or plastic material, said abradable cutting elements embedded in a material substantially softer than said ceramic or plastic material and separable from said softer material when acted upon by a force in the range of that necessary to cut dentin material with a hardness at or above the lower limit of hardness of said non-carious dentin.

15. The dental bur according to claim 12 wherein said abradable cutting elements comprise a hard ceramic or plastic material, said abradable cutting elements being deformable when acted upon by a force in the range of that necessary to cut dentin material with a hardness at or above the lower limit of hardness of said non-carious dentin.

16. The dental bur according to claim 1 wherein said cutting elements comprise outwardly projecting silicone rubber and said cutting elements deform when acted upon by a force in the range of that necessary to cut dentin material with a hardness at or above the lower limit of hardness of said non-carious dentin, and after deformation when said cutting elements are no longer acted upon by said force, said cutting elements recover to be outwardly projecting.

17. The dental bur according to claim 1 wherein said cutting elements are adapted to deflect, deform, or abrade upon encountering material having a hardness at or above about 20 Knoop Hardness Number.

18. The dental bur according to claim 1 wherein said cutting elements are adapted to deflect, deform, or abrade upon encountering material having a hardness at or above about 60 Knoop Hardness Number.

* * * * *